United States Patent [19]

Mori et al.

[11] Patent Number: 4,529,603

[45] Date of Patent: Jul. 16, 1985

[54] PHARMACEUTICAL COMPOSITION AND METHOD FOR TREATMENT OF PSYCHOMOTOR EXCITEMENT

[75] Inventors: Tadashi Mori, Kyoto; Teruo Nakajima, Osaka, both of Japan

[73] Assignee: Sumitomo Chemical Company, Limited, Osaka, Japan

[21] Appl. No.: 604,965

[22] Filed: Apr. 27, 1984

[30] Foreign Application Priority Data

Sep. 22, 1983 [JP] Japan .................. 58-175581

[51] Int. Cl.$^3$ .................. A61K 31/12; A61K 31/195
[52] U.S. Cl. .................. 514/565; 514/567
[58] Field of Search .................. 424/330, 319

[56] References Cited

U.S. PATENT DOCUMENTS 3,920,728 11/1975 Hegedus .................. 424/319
4,330,558 5/1972 Suzuki .................. 424/319

FOREIGN PATENT DOCUMENTS 52-125630 10/1977 Japan .
1455049 11/1976 United Kingdom .
2106388 4/1983 United Kingdom .

OTHER PUBLICATIONS

Sano Bulletin of the Japanese Neurochemical Society, vol. 12, (1973), p. 96.
Puig, Naunyn-Schmiedeberg's Arch Pharmocal, vol. 281, pp. 443-445 (1974).
Bartholini, The Journal of Pharmacology and Experimental Therapeutics, vol. 193, pp. 523-532 (1975).
Porter, Life Science, vol. 11, part 1, pp. 787-795 (1972).

*Primary Examiner*—Stanley J. Friedman
*Attorney, Agent, or Firm*—Cushman, Darby & Cushman

[57] ABSTRACT

A therapeutic agent for the treatment of psychomotor excitement containing as an active ingredient of L- or DL-erythro-3-(3,4-dihydroxyphenyl)-serine with or without a decarboxylase inhibitor.

14 Claims, 3 Drawing Figures

PHARMACEUTICAL COMPOSITION AND METHOD FOR TREATMENT OF PSYCHOMOTOR EXCITEMENT

This invention relates to a therapeutic agent for treatment of psychomotor excitement which comprises L or DL-erythro-3-(3,4-dihydroxyphenyl)serine (which is referred to as "erythro-DOPS" hereinafter) with or without a decarboxylase inhibitor and a method for treatment of psychomotor excitement using the said agent.

The erythro-DOPS is hydroxyamino acid of the formula:

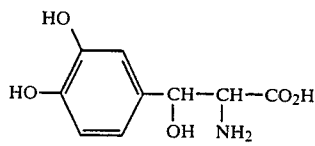

and a salt thereof is included in the invention.

Excessive psychomotor excitement is revealed as characteristic symptoms in several mental diseases. Typical examples are seen in the manic phase of manic-depressive illness and especially catatonic type of schizophrenia.

Therefore, this invention relates to the use of erythro-DOPS for improvement and treatment of symptoms of mania and catatonic type of schizophrenia, main symptom of which is psychomotor excitement.

Mania develops lasting euphoria or irritability, hyperthymia, flight or idea, elevation of ego feeling, etc. Such mental exaltations are said to be closely connected with the psychomotor excitement and there is the high possibility that they are different only in the mode of development but same in their causal mechanism.

Hitherto, various major tranquilizers have been used for the medical treatment of mania or manic state. Recently, lithium agents such as lithium carbonate and the like have been developed as therapeutic agents for mania. Furthermore, it has been found that carbamazepine has an antimanic effect.

In many cases, major tranquilizers are used for the treatment of catatonic type of schizophrenia.

However, these medicines or medical treatment with these medicines have some problems and are not always satisfactory. Chloropromazine, levomepromazine (phenothiazine agents), haloperidol (butyrophenone agents), etc. which have strong tranquilizing effects are often used as the major tranquilizers. Treatments with these medicines sometimes result in unnatural or excessive tranquilizing effects or cause various harmful side effects (e.g., extra-pyramidal syndroms).

On the other hand, the lithium agents which are used for the treatment of mania have an advantage of very natural tranquilizing effects.

It is necessary, however, to conduct general tests of blood and urine and examination of heart of patients before administration of the lithium agents and to exclude those who have heart disease and renal disease. Moreover, patients who are in the initial stage of pregnancy or in a period of lactation must also be excluded from treatment because of teratogenic action of the lithium agents.

Furthermore, at the administration of lithium carbonate, consideration must be given to avoid poisoning by lithium. It is said that lithium poisoning will occur when blood has continuously a lithium concentration of 2.0 mEq/l or more, but the poisoning may occur even if the concentration in blood is less than the said value. Therefore, it is always necessary to make measurement of lithium concentration in blood and to observe carefully clinical symptoms.

Treatment with lithium carbonate requires 3-8 days before a noticeable effect and besides the action is mild as compared with the major tranquilizers. Therefore, in some cases, the effects cannot be expected by the administration of lithium carbonate alone and in these cases, it must be administered in combination with a major tranquilizer. Furthermore, since manic patients generally lack to know their own disease, have elevated ego feeling and cannot accept therapeutical advices, it is difficult to lead them into medical care.

For these reasons, medicines and method of treatment which have more favourable effects for mania have been demanded.

For the same reasons, more preferable medicines for treatment of catatonic type of schizophrenia have also been demanded.

As a result of the inventors' extensive researches on novel medicines having an suppressing effect on psychomotor excitment or abnormal excitement of psychotic state seen in mania and in catatonic type of schizophrenia, it has been found that erythro-DOPS has the action to meet this purpose.

3-(3,4-Dihydroxyphenyl)-serine is an aromatic amino acid which may be called "DOPS" for short and includes threo form (threo-DOPS) and erythro form (erythro-DOPS) due to difference in steric configuration, each of which has optical isomers.

That is, DOPS has the four stereo-isomers, L-threo-DOPS and D-threo-DOPS and L-erythro-DOPS and D-erythro-DOPS and furthermore each of the threo-DOPS and the erythro-DOPS includes racemic form (DL form) which is a mixture of D form and L form in an equal amount.

It is known that L-DOPS undergoes a decarboxylation reaction by an aromatic L-amino acid decarboxylase in vivo to be converted to noradrenaline (referred to as "NA" hereinafter). Moreover, it has also been reported that L-threo-DOPS is converted to l-NA which is a biological active natural form and L-erythro-DOPS to d-NA which is a biological inactive unnatural form.

Several studies have also been made on pharmacological effects of DOPS. That is, it has been reported based on animal experiments that erythro- or threo-DOPS has an antihypertensive or antidepressive effect (U.S. Pat. No. 3,920,728) and that threo-DOPS has an inhibitory effect on harmaline induced tremor (Japanese Patent Publication (unexamined) No. 125630/1977).

Furthermore, it has been reported that threo-DOPS was clinically effective for the treatment of orthostatic hypotension (U.S. Pat. No. 4,330,558) or freezing phenomenon in parkinson's disease (UK Patent Publication No. 2106388 published on Apr. 13, 1983).

The inventors have administered erythro-DOPS to animals to examine the pharmacological effects thereof. As a result, it has been found that the erythro-DOPS suppresses psychomotor excitement as shown in Experimental Examples 1 to 3 given hereinafter.

Considering that the psychomotor excitement is the main symptom to characterize mania and catatonia, it can be said that there has been found the use of erythro- DOPS for improvement and treatment of mania and catatonia.

It is considered that the suppressing effects or erythro-DOPS on the psychomotor excitement according to this invention are based on the following action.

The inventors have also biochemically studied the change of contents of amines in the brain (NA, dopamine, serotonin) when erythro-DOPS is administered to animals. As a result, it has been found that only NA significantly increases as shown in Experimental Examples 4 and 5. The increase of the NA content is considered due to d-NA (unnatural form) from L-erythro-DOPS produced by the action of the aromatic L-amino acid decarboxylase in brain.

Considerable clinical researches hitherto have been made on the relation between mania or manic state and monoamines in the brain, and acceleration of metabolic turnover of NA (natural form) in the central nervous system is observed in manic state.

Thus, general view is that mania and manic state have correlation with excitation of the central nervous system.

Therefore the suppressing effect of erythro-DOPS on the psychomotor excitement may be interpreted as follows; d-NA in the brain produced from the administered erythro-DOPS would act to suppress the excitation of the central noradrenergic neuron system.

The suppressing effect of erythro-DOPS on the central noradrenergic neuron system has been found by the present inventors as shown in Experimental Example 6, in which the ptosis induced by tetrabenazine is enhanced by the administration of erythro-DOPS. It has been already reported that the tetrabenazine induced ptosis was produced by the decease in the activity of the central noradrenergic neuron system. This result would support the proposed mechanism stated above.

It has also been found by the present inventors that the effects of erythro-DOPS stated above are significantly enhanced by combination use of a peripheral decarboxylase inhibitor (referred to as "DCI" hereinafter) such as benserazide or carbidopa as shown in Experimental Example 6.

This finding indicates that DCI can inhibit the decarboxylation of erythro-DOPS in the peripheral system, and thus more erythro-DOPS can penetrate through blood-brain-barrier into the cerebral parenchyma.

The erythro-DOPS in this invention should be a substrate of an aromatic L-amino acid decarboxylase, and thus the erythro-DOPS used in this invention includes L- or DL-erythro-DOPS which can be prepared by the known method.

This invention will be explained in more detail below.

FIG. 1 shows the effect of DL-erythro-DOPS on quantity of spontaneous movement of mice, FIG. 2 shows the effect of DL-erythro-DOPS on quantity of spontaneous movement of mice increased by administration of methamphetamine and FIG. 3 shows the effect of DL-erythro-DOPS on quantity of spontaneous movement of mice administered with tranylcypromine.

EXPERIMENTAL EXAMPLE 1

Three mice as one group were put in a movement measuring box of Animex and quantity of spontaneous movements of the mice were measured at given intervals of time.

The mice put in the movement measuring box took searching behavior and showed high spontaneous movement quantity. Thereafter, they gradually became calm and crouched after about 30–40 minutes resulting in much decrease in their spontaneous moving quantity. $\beta$-phenylisopropylhydrazine hydrochloride (Catron, trade name) (referred to as "PIH" hereinafter) which is a monoamine oxidase inhibitor (MAOI) was intraperitoneally administered to the mice in an amount of 50 mg/kg. The above experiment was conducted on the mice after a lapse of 16 hours from the administration to find that there were tendencies of increase in the spontaneous movement quantity and increase in time required before the mice became calm.

Figure 1:
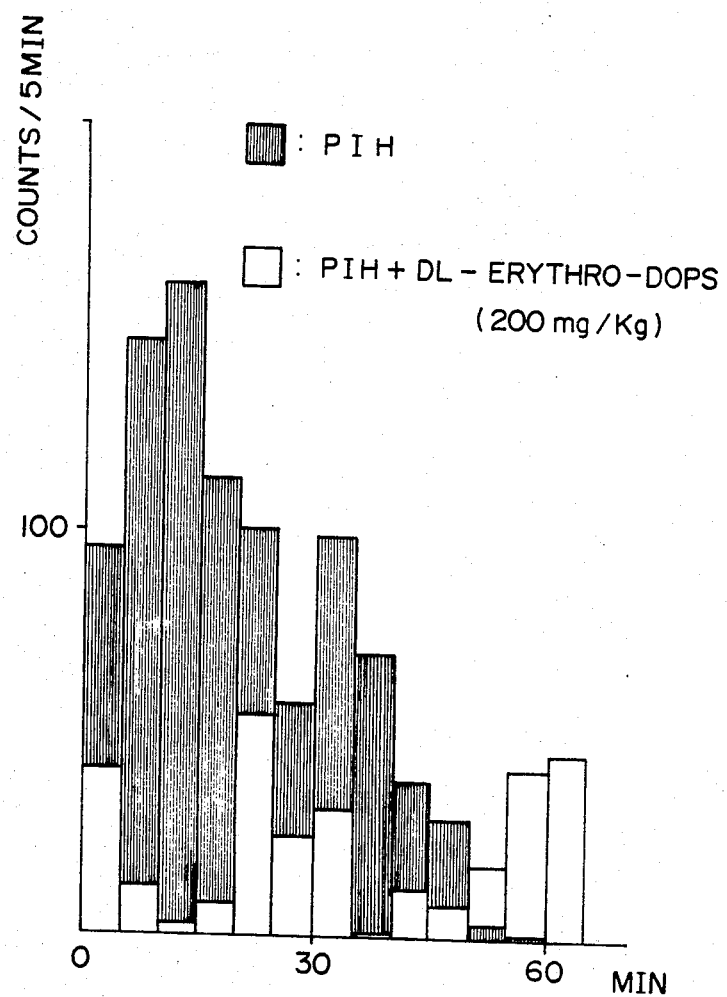
FIGS. 1–3 are graphs which show the effects of erythro-DOPS used in this invention.

Separately, 200 mg/kg of DL-erythro-DOPS was intraperitoneally injected to the mice and the effects thereof were examined. As shown in FIG. 1, conspicuous decrease in the quantity of spontaneous movement of the mice was recognized.

In FIG. 1 the axis of ordinates indicates the quantity of movement (counts/5 min.) and the axis of abscissae indicates the time (minute) from the beginning of measurement of the quantity of spontaneous movement which was after 30 minutes from administration of DL-erythro-DOPS.

▥ shows the results when only PIH (50 mg/kg) was intraperitoneally administered and □ shows the results when DL-erythro-DOPS (200 mg/kg) was intraperitoneally administered to the mice pretreated with the PIH.

EXPERIMENTAL EXAMPLE 2

The same experimental system of measuring spontaneous movement quantity of mice as used in Experimental Example 1 was employed in this Example. When methamphetamine (1.4 mg/kg) which is a stimulant was intraperitoneally administered to mice, the quantity of spontaneous movement abruptly increased and began to decrease after 50 minutes from the injection and they were restored to nearly the former state after 2 hours.

Figure 2:
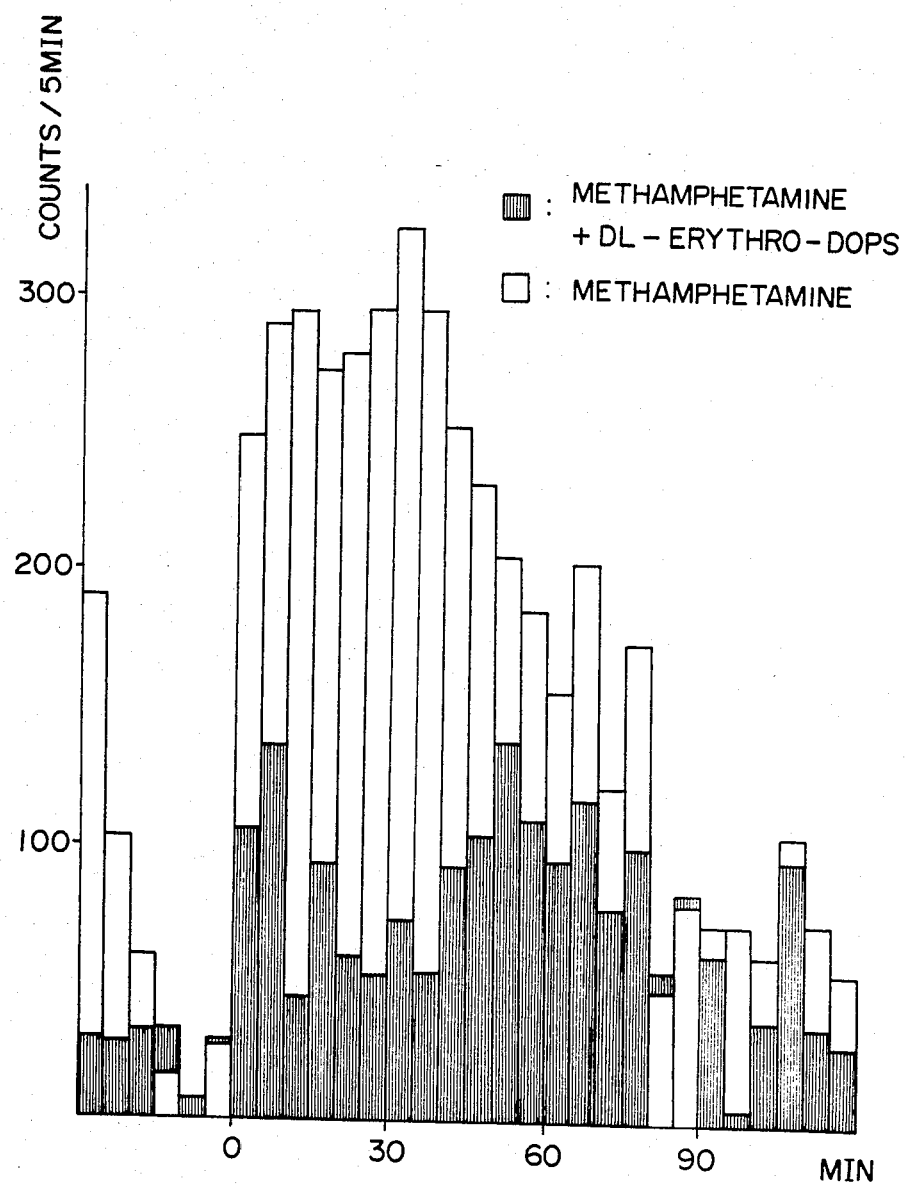

On the other hand, when DL-erythro-DOPS (200 mg/kg) was intraperitoneally administered together with said methamphetamine, increase of the quantity of movement is not noticeable and the action of methamphetamine to increase the quantity of spontaneous movement was retrained as shown in FIG. 2.

In FIG. 2, the axis of ordinates indicates the quantity of spontaneous movement and the axis of abscissa indicates the time (minute) when the time at which the administration of methamphetamine (1.4 mg/kg) alone or methamphetamine with DL-erythro-DOPS (200 mg/kg) was carried out was taken as zero point.

□ shows the results when only methamphentamine was administered and ▥ shows the results when methamphetamine and DL-erythro-DOPS were administered together.

EXPERIMENTAL EXAMPLE 3

The same experimental system of measuring the quantity of spontaneous movement of mice as used in Experimental Example 1 was used in this Example.

When 50 mg/kg of tranylcyromine which is MAOI and has the similar stimulant effect as amphetamine was intraperitoneally administered to mice, the spontaneous movement of the mice gradually increased and reached maximum in 120 minutes after administration and this quantity of movement was maintained.

On the other hand, when DL-erythro-DOPS was administered after 180 minutes, the quantity of movement began to decrease after about 20 minutes and this decrease continued for 30-90 minutes. Then, it began to gradually increase and returned to the original increased state as shown in FIG. 3.

Figure 3:
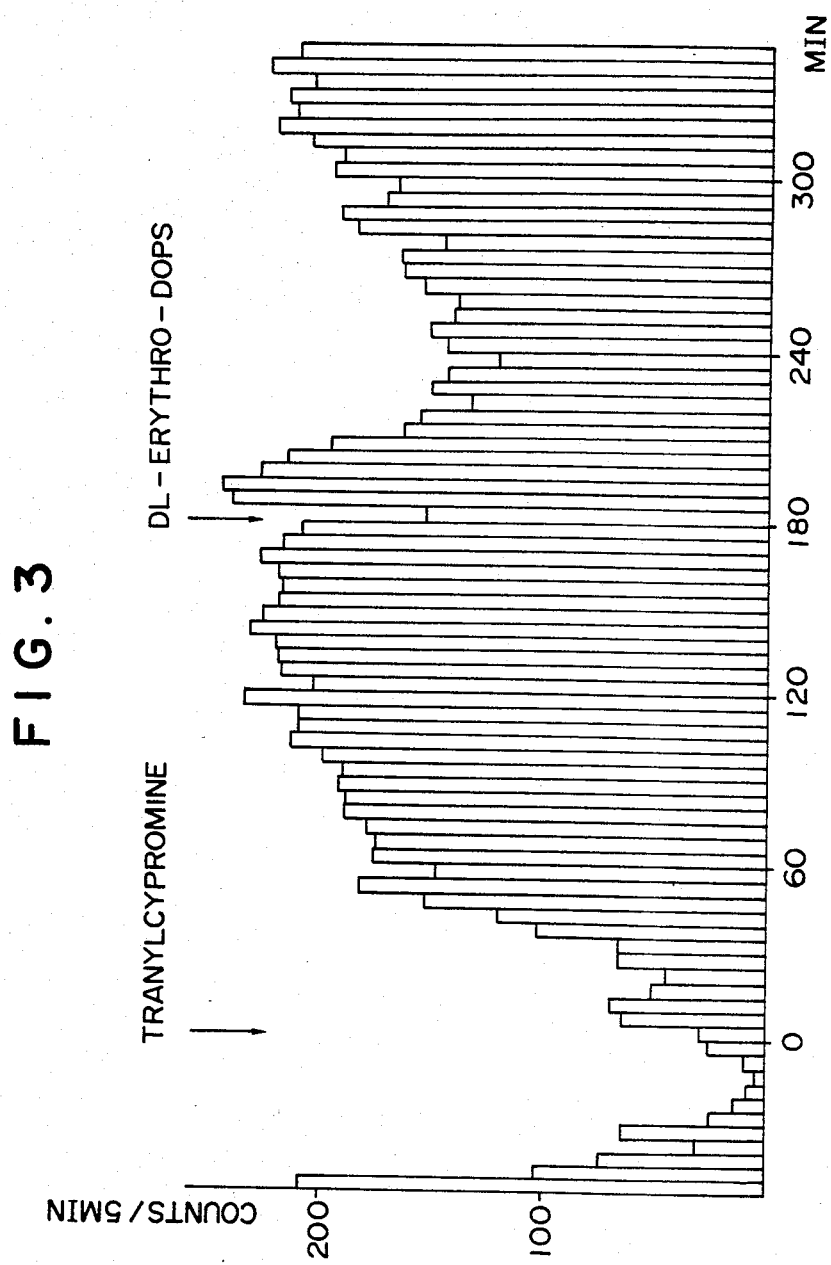

In FIG. 3, the axis of ordinates indicates the quantity of spontaneous movement and the axis of abscissae indicates the lapse of time (minute) and the arrows indicate the time when administration was conducted.

EXPERIMENTAL EXAMPLE 4

A physiological saline or PIH (50 mg/kg) was intraperitoneally injected to mice and content of amine in the brain was measured after 17 hours.

The measurement was substantially in accordance with the method of Ogasawara et al (J. Chromatography 180, 119). The content was expressed as ng/g wet weight and shown as mean value of the three mice ±SD.

| Amine content in the brain of PIH administered mice | | | |
|---|---|---|---|
| Administration | Noradrenaline (NA) | Dopamine | Serotonin |
| Physiological saline | 365 ± 25 | 791 ± 57 | 399 ± 47 |
| PIH | 1085 ± 79* | 1026 ± 122** | 1260 ± 39* |

*: $P < 0.005$
**: $P < 0.05$

EXPERIMENTAL EXAMPLE 5

PIH (50 mg/kg) was previously administered to mice and after lapse of 17 hours, physiological saline or DL-erythro-DOPS (200 mg/kg) was intraperitoneally injected to the mice.

Amine content in the brain was measured after a lapse of 30 minutes from the injection.

The content was expressed as ng/g wet weight and shown as mean value of the three mice±SD.

| Amine content in the brain of mice administered with erythro-DOPS | | | |
|---|---|---|---|
| Administration | Noradrenaline (NA) | Dopamine | Serotonin |
| PIH + physiological saline | 832 ± 88 | 941 ± 56 | 942 ± 133 |
| PIH + DL-erythro-DOPS | 1476 ± 105* | 895 ± 52 | 821 ± 92 |

*: $P < 0.005$

EXPERIMENTAL EXAMPLE 6

L-threo-DOPS (100 mg/kg and 200 mg/kg) was intraperitoneally injected at the same time with the intraperitoneal injection of tetrabenazine (40 mg/kg) and at 1 hr. after the intraperitoneal injection of benserazide or carbidopa.

The score of ptosis was measured by the method of Fukushima et al. (Arch. Int. Pharmacodyn. Therp. 229 163 1977) at 3 hrs. after the injection of tetrabenazine.

Effects of L-erythro-DOPS alone and combination with benserazide or carbidopa on the ptosis induced by tetrabenazine.

| Drugs | N | Ptosis score (Mean ± S.E.) |
|---|---|---|
| Control | 6 | 1.0 ± 0.4 |
| L-erythro-DOPS 100 mg/kg i.p. | 6 | 2.0 ± 0.4 |
| L-erythro-DOPS 100 mg/kg i.p. + Benserazide 1 mg/kg i.p. | 6 | 2.4 ± 0.7 |
| L-erythro-DOPS 100 mg/kg i.p. + Carbi dopa 1 mg/kg i.p. | 6 | 2.7 ± 0.6 |
| L-erythro-DOPS 200 mg/kg i.p. | 6 | 2.3 ± 0.5 |
| L-erythro-DOPS 200 mg/kg i.p. + Benserazide 1 mg/kg i.p. | 6 | 2.7 ± 0.6 |
| L-erythro-DOPS 200 mg/kg i.p. + Carbidopa 1 mg/kg i.p. | 6 | 2.8 ± 0.3 |

The erythro-DOPS may also be used as pharmaceutically acceptable acid addition salts. That is, as the addition salt forming acids, mention may be made of inorganic acids such as hydrochloric acid, hydrobromic acid, sulfuric acid, etc. and organic acids such as fumaric acid, citric acid, tartaric acid, succinic acid, etc.

The erythro-DOPS which is an active compound in this invention may be administered orally or parenterally in a dosage suitable for respective necessity. That is, the compound in a therapeutic amount may be orally administered in the usual forms, e.g., tablets, capsules, syrups, suspensions, etc. Furthermore, it may be parenterally administered by injection of the compound in the form of liquids such as solutions, emulsions, suspensions, etc.

Furthermore, the said suitable forms may also be made by blending the active compound with acceptable common carriers, diluents, binders, stabilizers, etc. When it is used in the form of injection, buffers, dissolution assistants, isotonic agents may be added thereto.

The dosage and the number of administration of erythro-DOPS used in this invention vary depending on the form thereof for administration and the condition of the psychomotor excitement to be treated. For example, in the case of oral administration, 0.1-4 g/day of the compound may be administered to an adult once or in doses several times a day. In the case of intravenous injection, 0.1-2 g/day may be administered to an adult once or in doses several times a day.

DCI may be used in an amount of a certain range for erythro-DOPS and generally may be used in a molar ratio of 0.0025-0.5 to erythro-DOPS.

Toxicity of erythro-DOPS used in this invention is extremely low and $LD_{50}$ value for mice is at least 5 g/kg through oral administration.

What is claimed is:

1. A method for the treatment of psychomotor excitement which comprises administration of an effective amount of erythro-3,4-dihydroxyphenylserine to a patient suffering from psychomotor excitement which is a mania or catatonic type of schizophrenia to suppress the psychomotor excitement.

2. A method for the treatment of psychomotor excitement according to claim 1, wherein the erythro-3,4-dihydroxyphenylserine is the DL-isomer or L-isomer.

3. A method for the treatment of psychomotor excitement according to claim 1, wherein there is included a decarboxylase inhibitor which is a member selected from benzerazide and carbidopa.

4. A method for the treatment of psychomotor excitement according to claim 1, wherein the erythro-3,4-dihydroxyphenylserine is orally administered in an amount of 0.1 to 4 g per day.

5. A method for the treatment of psychomotor excitement according to claim 1, wherein the erythro-3,4-dihydroxyphenylserine is intravenously administered in an amount of 0.1 to 2 per day.

6. A method for the treatment of psychomotor excitement according to claim 3, wherein the decarboxylase inhibitor is used in an amount of 0.0025 to 0.5 mole to 1 mole of the erythro-3,4-dihydroxyphenylserine.

7. A method according to claim 1 wherein there is present a decarboxylase inhibitor selected from the group consisting of benzerazide and carbidopa in an amount effective to enhance the effect of the erythro-3,4-dihydroxyphenylserine.

8. A method according to claim 1 carried out in the absence of a decarboxylase inhibitor.

9. An agent for the treatment of psychomotor excitement which is a mania or catatonic type of schizophrenia which comprises erythro-3,4-dihydroxyphenylserine in an amount to suppress the pyschonotor excitement and a decarboxylase inhibitor selected from the group consisting of benzerazide and carbidopa in an amount effective to enhance the effect of erythro-3,4-dihydroxyphenylserine.

10. An agent for the treatment of psychomotor excitement according to claim 9, wherein the erythro-3,4-dihydroxyphenylserine is DL-isomer or L-isomer.

11. An agent for the treatment of psychomotor excitement according to claim 9, wherein the decarbonylase inhibitor is included in an amount of 0.0025 to 0.5 mole to 1 mole of the erythro-3,4-dihydroxyphenylserine.

12. A therapeutic composition for use in the treatment of psychomotor excitement which is a mania or a catatonic type of schizophrenia which comprises an effective amount of L or DL-erythro-3,4-dihydroxyphenylserine as an active ingredient to suppress the psychomotor excitement and a pharmaceutically acceptable carrier or diluent.

13. A therapeutic composition for use in the treatment of psychomotor excitement which is a mania or a catatonic type of schizophrenia which comprises an effective amount of L or DL-erthro-3,4-dihydroxyphenylserine to suppress the psychomotor excitement and an effective amount of a decarboxylase inhibitor selected from the group consisting of benzerazide and carbidopa as an active ingredient to enhance the effect of the erythro,3,4-dihydroxyphenylserine and a pharmaceutical acceptable carrier or diluent.

14. A therapeutic composition for use in the treatment of psychomotor excitement according to claim 13, wherein the decarboxylase inhibitor is included in an amount of 0.0025 to 0.5 mole to 1 mole of the erythro-3,4,-dihydroxyphenylserine.

* * * * *